United States Patent [19]

Zaiger et al.

[11] Patent Number: Plant 5,308

[45] Date of Patent: Oct. 30, 1984

[54] APRICOT TREE (48-G-472)

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 472,628

[22] Filed: Mar. 7, 1983

[51] Int. Cl.[3] ..... A01H 5/03

[52] U.S. Cl. ..... Plt./39

[58] Field of Search ..... Plt./39

*Primary Examiner*—Robert E. Bagwill

*Attorney, Agent, or Firm*—Roger B. Webster

[57] ABSTRACT

A new and distinct variety of apricot tree which is of large size, vigorous, medium dense, and upright; foliated with medium size, ovate to orbicular, pointed leaves having a coarsely serrate margin; blooms from medium size, plump buds; the flowers being of medium size and white tinged with pink; and is a regular and productive bearer of large size, firm flesh, early and uniformly ripening, well distributed, freestone, globose fruit somewhat compressed laterally toward the suture.

1 Drawing Figure

BACKGROUND OF THE VARIETY

1. Field of the Invention

In the field of plant genetics we conduct an extensive and continuing plant breeding program including the origination and asexual reproduction of orchard trees, and of which peaches, apricots, and plums are exemplary. It was against this background of our activities that the present variety of apricot tree was originated and asexually reproduced by us in an experimental orchard located at Modesto, Stanislaus County, Calif.

2. Classification of the Variety

The present new and distinct variety of apricot tree is embraced by Class 39, Plants, of the U.S. Patent Office Manual of Classification.

3. Prior Varieties

Among the existent varieties of apricot trees which are known to us, and mentioned herein, are Flaming Gold (U.S. Plant Pat. No. 2,822) and King Cot (unpatented).

ORIGIN OF THE VARIETY

The present variety of apricot tree was originated by us, in the aforesaid experimental orchard, as a cross between a selected seedling of Flaming Gold and King Cot. A first generation seedling of such cross was grown under careful and continuing observation, and—upon such seedling (of said cross) evidencing, in maturity, especially novel and distinct characteristics—it was asexually reproduced in contemplation of potential commercialization.

ASEXUAL REPRODUCTION OF THE VARIETY

The present variety of apricot tree was asexually reproduced, in the aforesaid experimental orchard, by budding, and such reproductions ran true to the original tree and its fruit in all respects.

SUMMARY OF THE VARIETY

The present variety of apricot tree is, characteristically, large size, vigorous, medium dense and upright; foliated with medium size, ovate to orbicular, pointed leave having a coarsely serrate margin; blooms from medium size, plump buds; the flowers being of medium size and white tinged with pink; and is a regular and productive bearer of large size, firm flesh, early and uniformly ripening, well distributed, freestone, globose fruit somewhat compressed laterally toward the suture.

The present variety of apricot tree is further and more particularly characterized as follows:

In comparison to the Flaming Gold, the fruit of the present variety is larger, and is more uniform in ripening and distribution throughout the tree.

In comparison to the King Cot, the tree of the present variety is a more consistent bearer and has greater production.

Additionally, the fruit of the present variety continues, after picking at shipping ripe, to mature and increase in soluble solids (sugar); will hold in marketable condition for three weeks in cold storage; is of good fresh-fruit eating quality; ships well to long distance markets; and, when processed as dried fruit, maintains excellent color and flavor.

BRIEF DESCRIPTION OF THE DRAWING

The drawing comprise illustrations, by photographic reproduction in color, of typical specimens of the foliage and firm-ripe fruit of the present variety of apricot tree; such illustrations being of a twig with leaves, and separate fruit; one of the latter being cut in half to expose the flesh, with the stone remaining in one of the halves.

DESCRIPTION OF THE VARIETY

The botanical details of this new and distinct variety of apricot tree—with color definitions (except those in common color terms) referenced to Reinhold Color Atlas by A. Kornerup and J. H. Wanscher—are as follows:

TREE

Size: Large.
Vigor: Vigorous.
Density: Medium.
Form: Upright.
Production: Productive.
Bearing: Regular.

TRUNK

Size: Stocky.
Texture: Shaggy.

BRANCHES

Size: Stocky to medium.
Color: Brown to reddish brown.
Lenticels: Medium size. Medium number.

LEAVES

Size: Medium.
*Average length.*—2½" To 3".
*Average width.*—2½" To 3".
Shape: Ovate to orbicular. Pointed.
Thickness: Medium.
Texture: Relatively smooth.
Petiole: Average length — 1".
Margin: Coarsely serrate.
Glands:
*Number.*—Variable — 1 to 6.
*Position.*—Distal on petiole and on base of blade.
Color:
*Upper surface.*—Deep green (28-E-8).
*Lower surface.*—Grayish green (28-D-5).

FLOWER BUDS

Size: Medium.
Length: Medium to short.
Shape: Plump.

FLOWERS

Size: Medium.
Color: White with tinge of pink.
Pubescence: Pubescent.
Blooming period:
*Date of first bloom.*—Feb. 22, 1980.
*Date of full bloom.*—Mar. 2, 1980.
Pollen: Present.

FRUIT

Maturity when described: Firm ripe.
Date of first picking: June 3, 1980.
Date of last picking: June 10, 1980.
Size: Large.
*Average diameter axially.*—2½" To 2¾".
*Average transversely in suture plane.*—2½" To 3".
*Average diameter at right angles to suture plane.*—2¼" To 2½".
Form: Globose. Somewhat compressed laterally toward suture.
Suture: Shallow. Extends from stem to blossom end, slightly deeper at blossom end.
Cavity: Rounded to slightly elongated in suture plane.
*Average depth.*—3/16".
*Average breadth.*—5/16".
Base: Rounded to slightly retuse.
Apex: Rounded.
Pistil point: Slightly depressed.

SKIN

Thickness: Medium.
Texture: Medium.
Tendency to crack: None.
Down: Scant. Very short.
Color: Yellow (4-B-8 to 5-B-8).

FLESH

Ripens: Evenly.
Texture: Firm. Fine. Melting.
Flavor: Mild.
Eating quality: Good.
Color: Dark yellow (4-A-8) to Chrome yellow (5-A-8).

STONE

Type: Freestone.
Size: Large.
*Average length.*—1⅜".
*Average breadth.*—1".
*Average thickness.*—⅝".
Form: Ovoid.
Base: Straight.
Apex: Nearly rounded.
Surface: Regularly but only slightly pitted throughout.
Ridges: Two distinct ridges extending approximately 180° across surface of the stone on both sides of the surface plane and approximately 30° displaced from each other.
Tendency to split: None.
Color: Brown (6-E-8 to 7-E-8).

USE

Dessert; local and long distance markets; canning; drying.

KEEPING QUALITY

Very good.

SHIPPING QUALITY

Very good.

The apricot tree and its fruit herein described may vary in slight detail due to climatic and soil conditions under which the variety may be grown; the present description being of the variety as grown in the Central Valley of California.

We claim:

1. A new and distinct variety of apricot tree, substantially as illustrated and described, characterized, in particular, by fruit which is larger, and more uniform in ripening and distribution throughout the tree in comparison to the Flaming Gold; by more consistent bearing with greater production of fruit in comparison to the King Cot; and by fruit which is of good fresh-fruit eating quality, good storage quality, ships well to long distance markets, and maintains excellent color and flavor when processed as dried fruit.

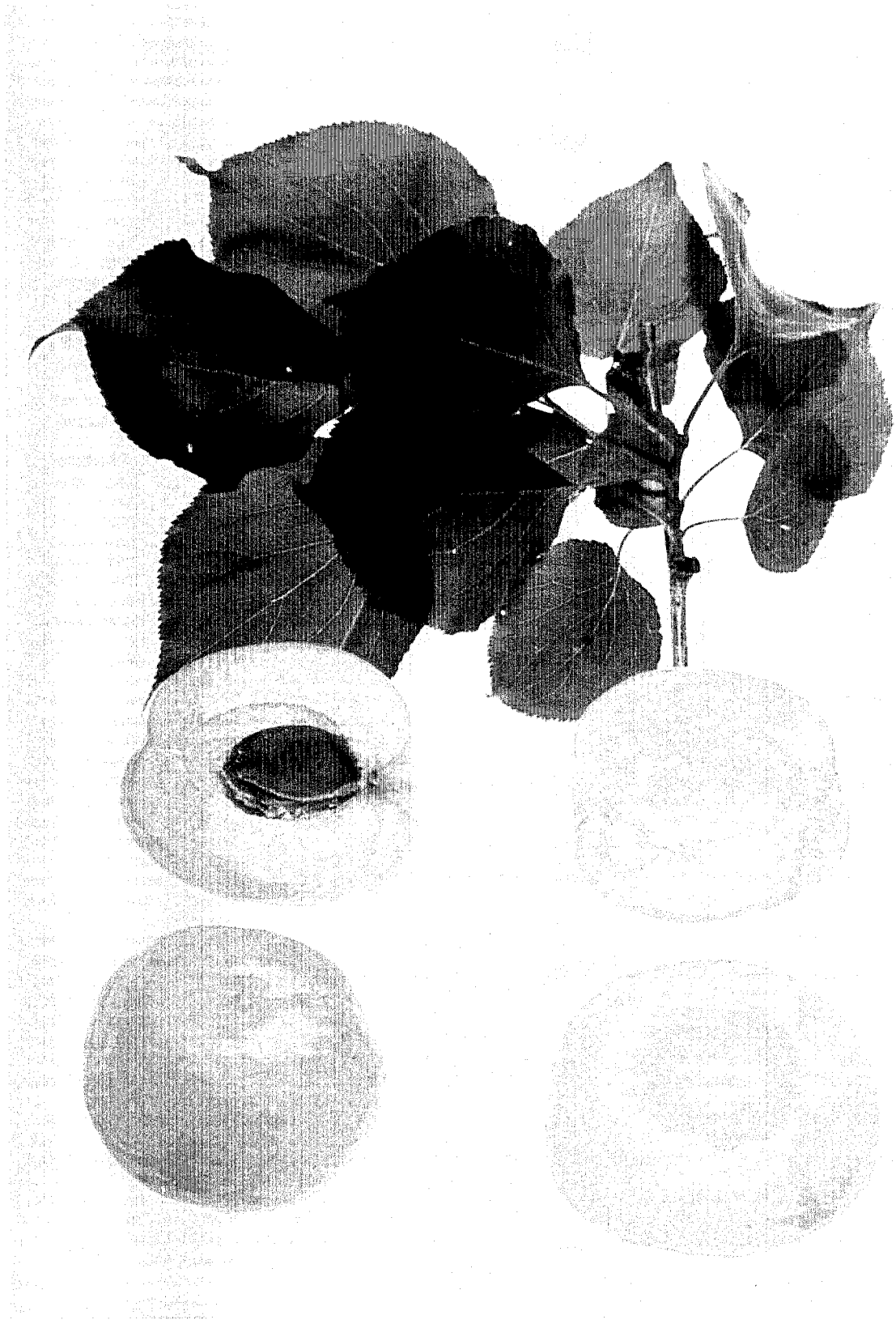

* * * * *